United States Patent [19]

Uchiyama et al.

[11] 4,202,631
[45] May 13, 1980

[54] APPARATUS FOR DETECTING DEFECTS IN PATTERNS

[75] Inventors: Yasushi Uchiyama, Yokohama; Daikichi Awamura, Kawasaki, both of Japan

[73] Assignee: Nippon Jidoseigyo Ltd., Kawasaki City, Japan

[21] Appl. No.: 922,217

[22] Filed: Jul. 5, 1978

[30] Foreign Application Priority Data

Jul. 14, 1977 [JP] Japan ................................. 52-83520

[51] Int. Cl.² ............................................. G01B 11/00
[52] U.S. Cl. ..................................... 356/394; 356/398
[58] Field of Search .......................... 356/394, 398, 71

[56] References Cited

U.S. PATENT DOCUMENTS

| 3,546,377 | 2/1970 | Troll ..................... 356/398 |
| 3,944,369 | 3/1976 | Cuthbert et al. ........... 356/394 |
| 4,123,170 | 10/1978 | Uchiyama et al. ......... 356/398 |

*Primary Examiner*—John K. Corbin
*Assistant Examiner*—R. A. Rosenberger
*Attorney, Agent, or Firm*—Stevens, Davis, Miller & Mosher

[57] ABSTRACT

An apparatus for detecting defects in patterns, particularly defects in chip patterns of photomasks for use in manufacturing semiconductor integrated circuits comprising an optically scanning means for scanning identical portions of the two patterns to be compared with each other with a pair of scanning light spots to produce a pair of picture signals each corresponding to a respective one of the scanned pattern portions; and a defect detecting section for receiving said pair of picture signals and producing a defect signal as a difference between the two picture signals. In order to remove pseudo-defects which appear in the vicinity of contours of the patterns mainly due to registration error between the two patterns there are further provided a contour signal producing section for receiving at least one of said pair of picture signals to produce a contour signal having a given width and a control section for receiving said contour signal and decreasing a defect detection sensitivity in the vicinity of the pattern contours. In an embodiment of the control section it comprises a gate which is controlled by the contour signal in such a manner that the defect signal from the defect detecting signal is blocked by the gate while the contour signal is supplied from the contour signal generating section. In this embodiment the sensitivity for defect detection in the vicinity of the contours of patterns is decreased to zero.

24 Claims, 29 Drawing Figures

Pattern A

Pattern B

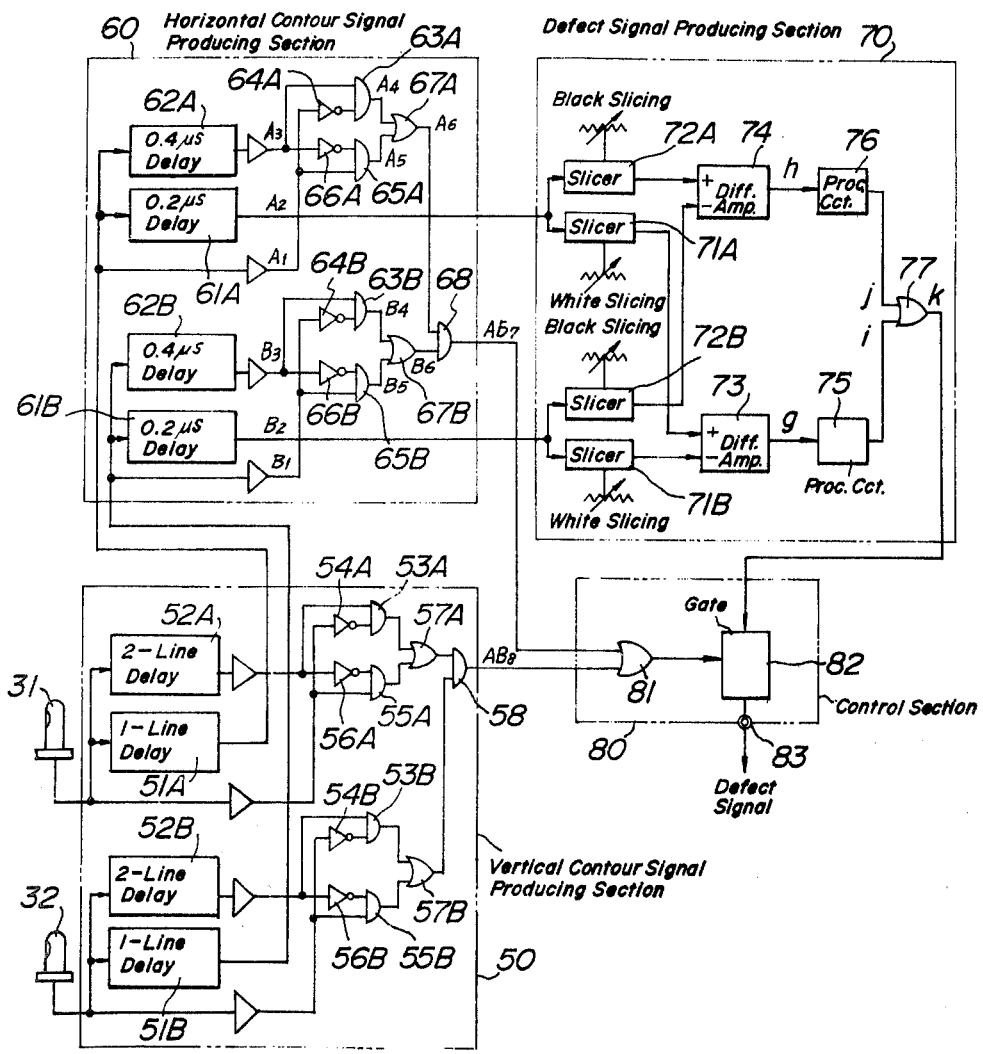

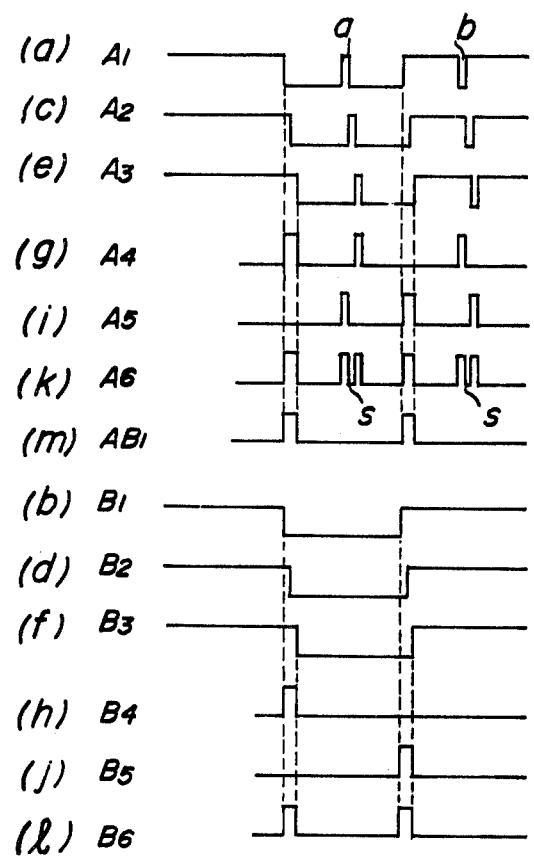
FIG_12

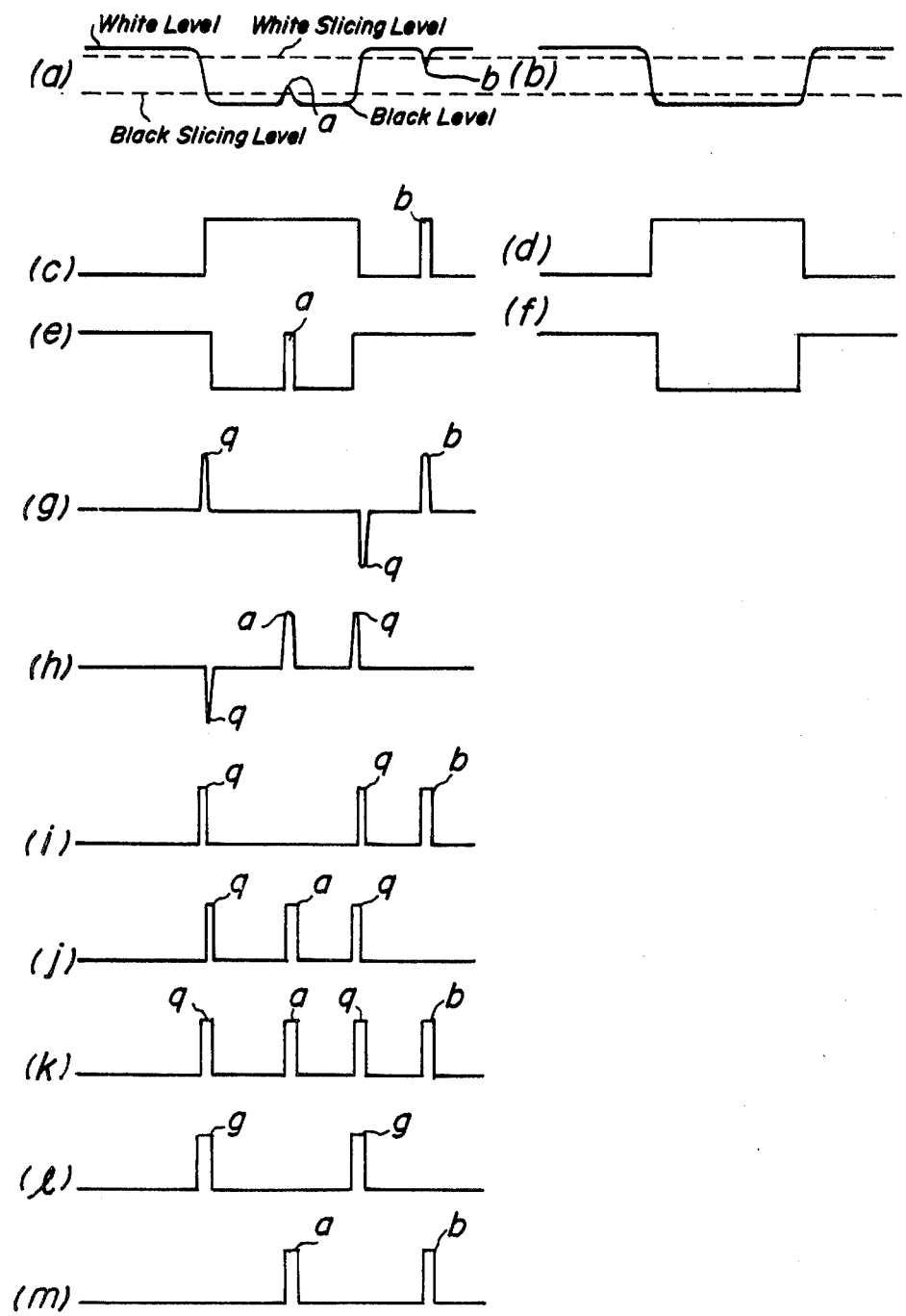

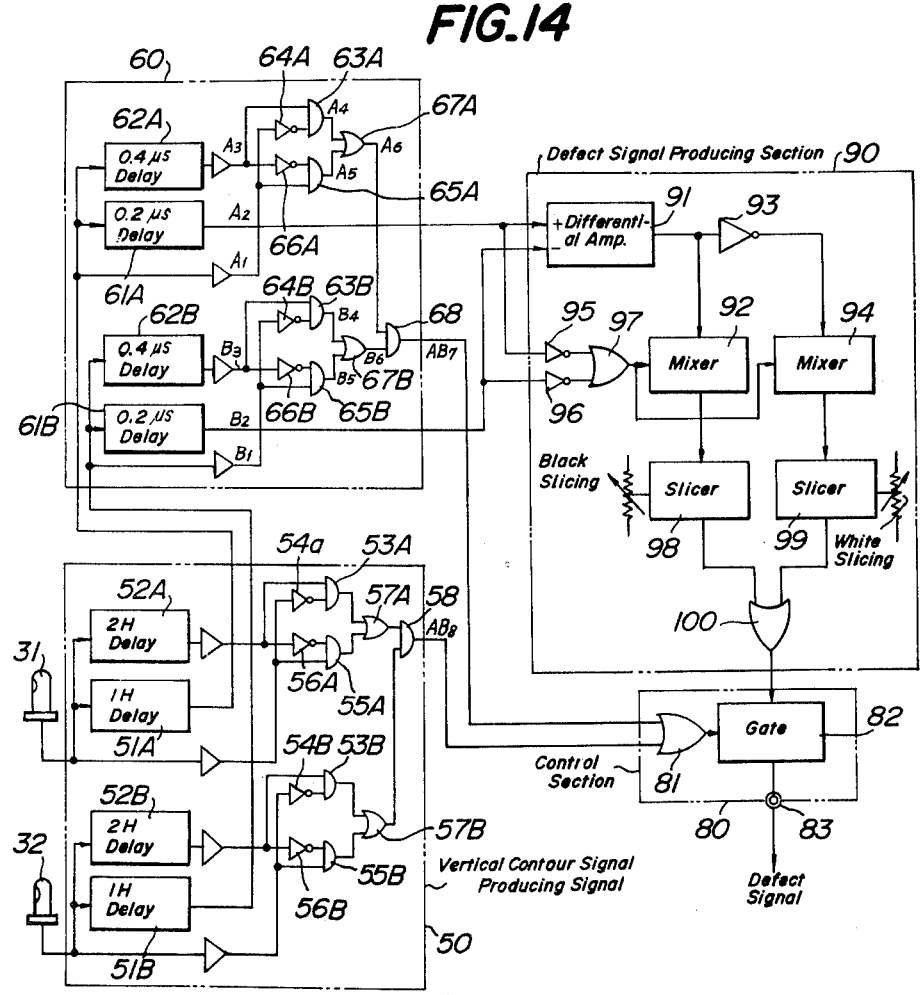

FIG_18

APPARATUS FOR DETECTING DEFECTS IN PATTERNS

BACKGROUND OF THE INVENTION

1. Field of the Invention

The invention relates to an apparatus for detecting defects in patterns, particularly defects in chip patterns of photomasks for use in manufacturing semiconductor integrated circuits.

2. Description of the Prior Art

In processes of manufacturing integrated circuits there is a process for photoetching a silicon wafer. In this process a mask having a desired pattern is placed on a photolacquer layer applied on the silicon wafer and the photolacquer layer is irradiated by visible light or ultraviolet ray through the mask. Then the silicon wafer is selectively photoetched in accordance with the mask pattern. The defects in the mask having the pattern printed thereon might affect the yield of the manufactured integrated circuits. The mask is formed by depositing a metal film such as chromium on a glass plate having a sufficiently flattened surface and then by printing a desired pattern on the surface. If there are pin holes in the metal film, the printed pattern might have defects. The present inventors have developed an apparatus for detecting automatically such pin holes in the metal film of the mask pattern with high accuracy.

The photomask has various defects in its pattern as well as in the pin holes. The defect detecting apparatus according to the present invention is particularly suitable to detect such defects in the printed pattern of the photomask.

FIG. 1 shows schematically a photomask 1 which is used for manufacturing the semiconductor integrated circuits. In the mask 1 there are formed a number of identical chip patterns 3 which are divided by a number of orthogonal scribe lines 2.

FIG. 2 is a microscopic image of a part of the chip pattern 3. This part of the pattern has no defect and thus is a perfect one. The pattern is composed of transparent portions 4 and opaque portions 5. FIG. 3 is also a microscopic image of the corresponding part of another pattern which includes various defects. Portions A and B are residual parts of the metal film. At the portion A the residual part bridges two adjacent lands which should be separated from each other. Thus this residual portion A should be detected as a real or true defect. While the other residual portion B exists in a space and in most cases this portion B might not injure the integrated circuits. At a portion C a part of a land is lacking. However, this land is not completely separated and thus this porton C might not affect the integrated circuits. At a portion D a land is completely cut away and this causes serious influence on the integrated circuits.

Up-to-date there have been developed the following methods for detecting the above mentioned defects in the mask pattern.

(1) The mask is inspected by means of a microscope so as to find the defects. In general the pattern is formed by straight lines which intersect perpendicularly with each other, whilst the most defects have irregular shapes as shown in FIG. 3. Therefore the defects can be found in a relatively easy manner. However, this method requires a lot of time and labor work and thus is not suitable for detecting the defects in the photomask used in manufacturing the integrated circuits which has a number of chip patterns.

(2) As shown in FIG. 4 a sample mask 7 which has a perfect pattern is prepared and images of this sample mask 7 and the mask 6 to be tested are inspected in a superimposed manner. In this case the image of the mask 6 to be tested is colored in red and the image of the sample mask 7 is colored in green which is complementary to red. For this purpose there is arranged a red color light source 9 and the mask 6 to be tested is irradiated by red light emitted from the source 9. The red light passing through the mask 6 is made incident on an inspection eye 14 by means of an objective 10, a mirror 11, a half mirror 12 and an eye piece 13. The sample mask 7 is illuminated by a green light source 15 and the green light passing through the sample mask 7 is made incident upon the inspection eye 14 by means of an objective 16, a mirror 17, a half mirror 18 and the eye piece 13. When the sample mask 7 having no defect as shown in FIG. 2 and the test mask 6 having the defects as illustrated in FIG. 3 are inspected in a superimposed manner, the portions A and B are seen in green, because in these portions only the green light from the sample mask 7 reaches the inspection eye 14. The portions C and D are seen in red, because in these portions only the red light from the mask 6 reaches the eye 14. The transparent portion other than the portions A, B, C and D can be seen in white, because in the transparent portion both the green and red light rays from the masks 6 and 7, respectively reach simultameously the inspection eye 14. The opaque portion 5 is seen, of course in black. The defect portions are seen in green or red and the portions having no defect are seen in black or white. Thus the defects can be found in a simpler manner. The mask used in manufacturing the integrated circuits have formed therein a number of identical chip patterns and in order to check such a mask it is necessary to arrange the mask 6 to be tested and the sample mask 7 on a same carrier stage 19 and to move this carrier stage 19 slightly so as to check the successive chip patterns. In case of inspecting the two images of the masks 7 and 6 in the superimposed manner two images must be aligned accurately. If there is an error in this alignment it is impossible to detect the defects accurately. In particular when the two masks 6 and 7 are placed on the same table 19, the masks must be aligned with X and Y directions of the movement of the table. If there is an error in this alignment, the error in superimposition of the two images will increase in accordance with the movement of the table 19. A play in the carrier table 19 also affects the superposition of the two images. Moreover since this method is effected with the naked eye, the inspector might be tired and errors caused by the human beings could not be avoided. Also long time period is required for inspection.

(3) Electric signals corresponding to a sample pattern which does not include a defect have been previously stored in a record medium such as a magnetic tape or memory elements with using an electronic computer. The image of the mask to be tested is picked up by means of a microscopic television camera to produce a video signal. This video signal is compared with the previously stored signal of the sample pattern so as to detect the defects in the checked mask. This method has an advantage that the defects can be detected automatically without using the eyes of the human beings. However an apparatus for carrying out such a method is liable to be very large and complicated in construction and thus the apparatus becomes quite expensive.

In order to avoid the disadvantages mentioned above the inventors have designed an apparatus comprising a single camera tube on which images of identical portions of two patterns to be checked are focussed in a superimposed manner and defects in the patterns are detected by detecting an amplitude of the output video signal from the camera tube. In this apparatus the defects are represented as gray tones in the video signal and the gray tones are detected by means of an amplitude limiter. However the accuracy of the defect detection was low, because the fluctuation of the amplitude of the video signal is large. In order to obviate this disadvantage the inventors have further developed a method in which use is made of two camera tubes on each of which a respective image of the two patterns is formed and defects in the patterns are detected by comparing two output video signals from the two camera tubes. In this method the accuracy of the defect detection could be raised to a great extent as compared with the method in which only the single camera tube is used. However it has been found that it is quite difficult to make the operations of the two camera tubes identical with each other. Moreover in case of using the camera tube the carrier table on which the masks to be compared are placed must be transported intermittently due to the residual image effect of the camera tube. This results in a very complicated driving mechanism for the carrier table. The operation speed of the camera tube is rather slow and a time period of 70 to 100 ms is required for checking each field of view. Therefore a quite long time is required for detecting the defects in a number of patterns of the mask.

The inventors have further devised a checking apparatus which can avoid all of the above mentioned drawbacks and check the defects in patterns accurately and speedily with a simple construction. This apparatus comprises means for producing a scanning light spot, an optical system for directing said spot onto two identical portions of patterns to be compared with each other, a pair of light receiving devices each receives a light transmitted through or reflected from respective pattern portions, circuit means for inverting a phase of an output signal supplied from one of said two light receiving devices and circuit means for mixing the phase inverted output signal and a non-inverted output signal from the other light receiving device. According to such an apparatus the adjacent patterns 3 formed in the photomask 1 shown in FIG. 1 for use in manufacturing the integrated circuits can be compared with each other and defects can be detected with high accuracy. After various experiments it has been further found that the pattern might be detected as defect one even when relative position of two patterns to be compared with each other deviates slightly and/or these patterns are different from each other only slightly. This results in that masks are unnecessarily rejected as defective masks. That is to say the slight deviation of patterns and/or slight difference in patterns are detected as defects even if they do not affect the manufacture of integrated circuits and thus such mask should not be identified as defective one.

Reasons for producing the above mentioned pseudo-defects may be summarized as follows:

(1) A pair of lens systems for forming two images of two patterns to be compared have different distortion characteristics.

(2) A stage for carrying the mask having the patterns to be compared rotates slightly during the travelling and thus two images deviate slightly with respect to each other.

(3) A distance or pitch between the successive chips has error (about 0.5 μm) due to less accuracy of a repeater for use in manufacturing the photomasks.

(4) Contours of the pattern images fluctuate due to noise in the picture signals.

(5) If the glass plate of the photomask has less plainness, the two lens systems cannot be simultaneously focussed correctly.

Among the above mentioned causes the first and third ones are important or serious. But the problem with respect to the repeater has been improved because nowadays fine patterns have been required and the deviation in chip pitch can be made very small.

The inventors have further devised an improved checking apparatus which can effectively remove the pseudo-defects which should not be detected as true defects. This apparatus is disclosed in U.S. Patent Application Ser. No. 746,584 filed on Dec. 1, 1976 for which a notice for allowance has been issued. The apparatus comprises a pattern scanning device for scanning optically identical portions of two patterns to be compared with each other to produce corresponding picture signals, circuit means for subtracting one of the picture signal from the other picture signal to produce a difference signal denoting pattern differences, delay means for delaying the difference signal and circuit means for receiving said delayed difference signal and the non-delayed difference signal to produce an output defect signal in which any pseudo-defects having dimensions smaller than a given dimension determined by the delay time have been removed.

According to the last mentioned defect detecting apparatus as far as a vicinity of the contour of pattern is concerned patterns are compared with each other after their contours have been thinned by a predetermined length and thus the slight registration error and the small defects at the contours can be ignored. However since even in portions other than the vicinity of contours the same treatment is effected the true defects in these portions might be also removed. That is to say this detecting apparatus can remove the pseudo-defects only with the sacrifice of decrease of detection sensitivity. For example if the resolution of the whole apparatus including the optical system and electrical system is 1 μm and the contour is thinned by 1 μm, the effective resolution of apparatus is decreased to 2 μm, because only defects larger than two microns are detected, but defects smaller than 2 μm cannot be detected.

SUMMARY OF THE INVENTION

The present invention is based on the fact that since the pseudo-defects are produced almost in the vicinity of pattern contours the detection sensitivity can be decreased only in the vicinity of contours, but in portions of patterns other than the vicinity of contours it is not necessary to decrease the sensitivity and the apparatus can detect accurately true defects with the high sensitivity.

The present invention has for its object to provide a defect detecting apparatus which can effectively remove the pseudo-defects produced at the vicinity of contours of patterns to be compared with each other.

It is another object of the invention to provide a defect detecting apparatus which can detect true defects in pattern regions other than the contour regions with high sensitivity which the apparatus has inherently.

According to the invention an apparatus for detecting defects in patterns comprises an optical scanning device for optically scanning simultaneously identical portions of two patterns to be compared with each other to produce a pair of picture signals each corresponding to a respective one of the scanned pattern portions;

contour signal generating means for receiving at least one of said picture signals and producing a contour signal which represents contour regions of a predetermined width along contours of the patterns;

defect detecting means for receiving said pair of picture signals and producing a difference between these picture signals to generate a defect signal; and control means for receiving said contour signal and decreasing a defect detection sensitivity in said contour regions of patterns.

According to the invention defects in region of patterns other than said contour region can be detected with the high detection sensitivity, while the pseueo-defects appearing in the vicinity of contours of patterns can be effectively removed. This results in that the accuracy of detection can be increased without sacrificing the defect detection sensitivity.

BRIEF DESCRIPTION OF THE DRAWINGS

FIG. 11 is a block diagram showing an embodiment of a signal processing circuit of the defect detecting apparatus according to the invention;

FIGS. 12a to 12m are waveforms for explaining the operation of the circuit of FIG. 11;

FIGS. 13a to 13m are waveforms for explaining the operation of slicing circuits;

FIG. 14 is a block diagram depicting another embodiment of the signal processing circuit of the defect detecting apparatus according to the invention;

DESCRIPTION OF THE PREFERRED EMBODIMENTS

Figure 5:
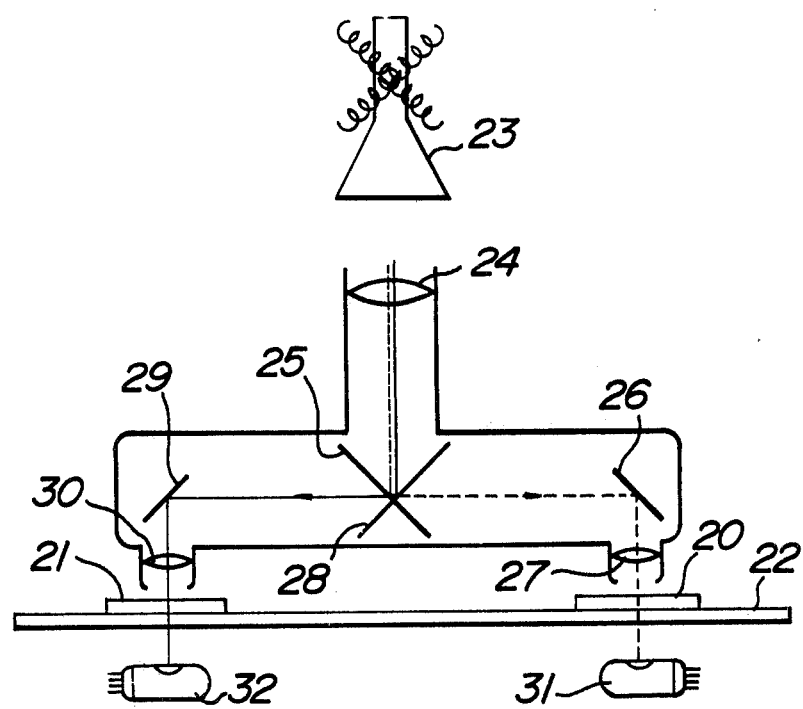
FIG. 5 is a schematic view showing an embodiment of an optical system of a defect detecting apparatus according to the invention.

FIG. 5 shows diagrammatically an embodiment of an optically scanning device provided in a defect detecting apparatus according to the invention. In this embodiment a mask 20 to be tested and a sample mask 21 having no defect are placed on a single carrier table 22. There is provided a flying spot cathode ray tube 23 and an image of a scanning raster formed by the flying light spot is focussed on the mask 20 by means of a lens 24, a half mirror 25, a mirror 26 and a lens 27 and on the mask 21 by means of the lens 24, a half mirror 28, a mirror 29 and a lens 30. The light passing through the mask 20 is received by a first photoelectric converter 31 and the light through the mask 21 is received by a second photoelectric converter 32. In this case the raster image of the flying spot scanner 23 should be projected on identical pattern portions of the masks 20 and 21. Therefore if the mask 20 does not include a defect in the related pattern portion, the electric output signals from the photoelectric converters 31 and 32 become identical with each other. But if the mask 20 has a defect, the two output signals are different from each other. Therefore by comparing these output signals the defects in the pattern on the mask 20 can be detected with the high accuracy.

In the above embodiment since the mask 20 and the sample mask 21 are placed on the same carrier table 22 and are moved in the orthogonal X and Y directions, the two masks have to be aligned accurately in the X and Y directions. If the two masks 20 and 21 are not aligned correctly or the carrier table 22 has a play, the scanned pattern portions of the masks 20 and 21 become different from each other with the movement of the carrier table 22 and thus the accurate defect detection could not be effected.

Figure 6:
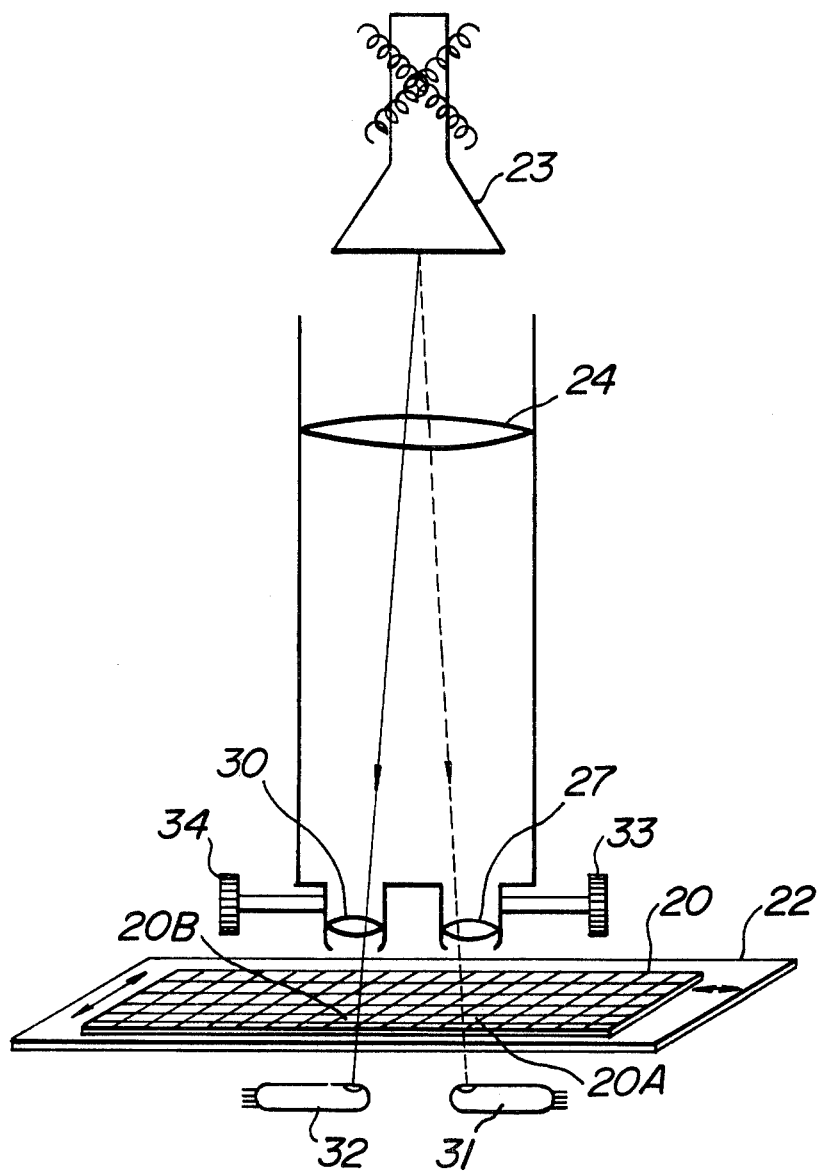
FIG. 6 is a schematic view illustrating another embodiment of the optical system of the defect detecting apparatus according to the invention.

FIG. 6 shows another embodiment of the optically scanning device of the defect detecting apparatus according to the invention. In this embodiment the disadvantage just mentioned above can be deleted. In FIG. 6 the same elements as those shown in FIG. 5 are denoted by the same reference numerals. In FIG. 6 only the mask 20 to be checked is placed on the carrier table 22. A scanning raster image of the flying spot scanner tube 23 is focussed on a part of a pattern 20A of the mask 20 by means of a common lens 24 and a first lens 27 and on a corresponding part of a pattern 20B which is near the pattern 20A by means of the common lens 24 and a second lens 30. In order to inspect the identical portions of the patterns 20A and 20B a distance between optical axes of the lenses 27 and 30 can be adjusted by means of adjusting handles 33 and 34. In the present embodiment the accuracy of the defect detection is little affected by a play of the carrier table 22, because the two patterns 20A and 20B situate quite near.

Figure 3:
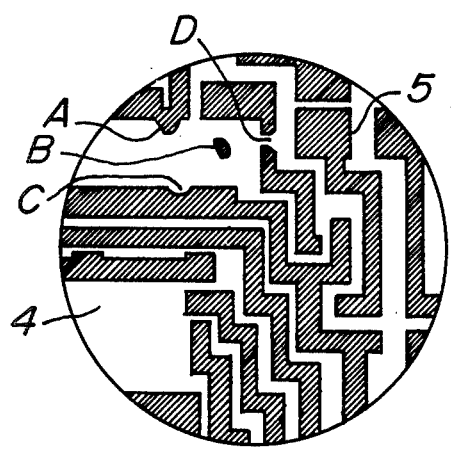
FIG. 3 is also a microscopic image of the same part of a photomask which includes various defects.
Figure 4:
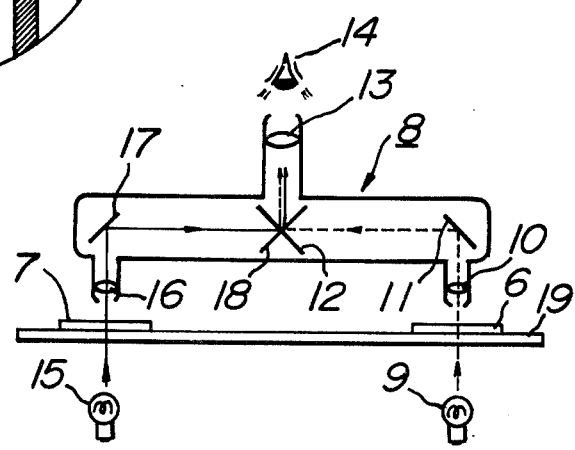
FIG. 4 is a schematic view illustrating a known defect detecting apparatus.
Figure 7:
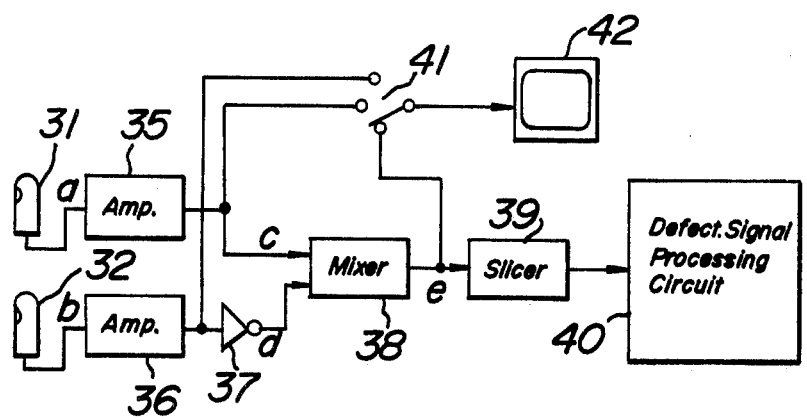
FIG. 7 is a block diagram showing an embodiment of electric circuit means of the defect detecting apparatus according to the invention.
Figure 8:
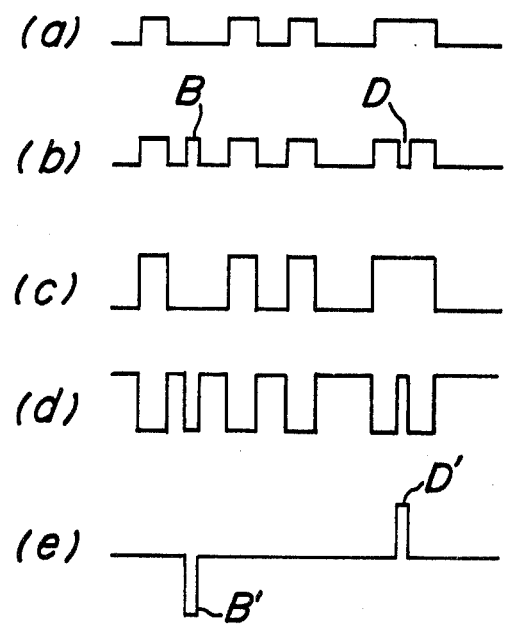
FIGS. 8a to 8e are waveforms for explaining the operation of the circuit means of FIG. 7.

FIG. 7 is a circuit diagram illustrating an embodiment of electrical circuit means of the defect detecting apparatus according to the invention. FIG. 8 is waveforms at various points of the circuit of FIG. 7. FIG. 8a shows a waveform of an output signal from the first photoelectric converter 31 which receives the scanning light spot passing through the pattern 20A and FIG. 8b illustrates a waveform of an output signal from the second photoelectric converter 32 which receives the scanning light spot passing through the pattern 20B. It is now assumed that one of the patterns 20A does not include a defect, but the other pattern 20B has defects. A pulse B in the waveform of FIG. 8b is produced by the defect B shown in FIG. 3 and a pulse D corresponds to the defect D in FIG. 3. The signal supplied from the first photoelectric converter 31 is amplified by an amplifier 35. The signal from the second photoelectric converter 32 is also amplified by an amplifier 36 and is then inverted by an inverter 37. The amplified signal (FIG. 8c) from the amplifier 35 and the amplified and inverted signal (FIG. 8d) from the inverter 37 are supplied to a mixer 38. An output signal from the mixer 38 is shown in FIG. 8e. As shown in the drawing the level of the mixer output signal corresponding to portions with no defect appears as a zero level, but the signal level differs from zero at portions of defects to produce pulses B' and D'. These defect pulses B' and D' have opposite polarities. These pulses are supplied through a slicer 39 to a defect detecting and process circuit 40. The output defect signal from the mixer 38 may be supplied to a monitor 42 through a switch 41 so as to inspect the condition of superimposition of the two patterns 20A and 20B. That is the user can adjust the handles 33 and 34 with inspecting the superimposed images of the patterns 20A and 20B on the monitor 42 and the two images can be registered completely. Moreover in order to inspect in detail any one of the images of the patterns 20A and 20B, any one of the output signals from the amplifiers 35 and 36 may be supplied to the monitor 42 through the switch 41.

Figure 1:
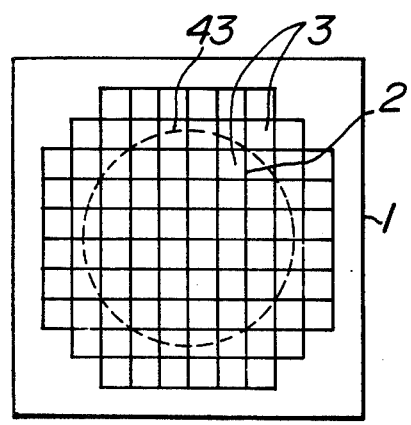
FIG. 1 is a plan view showing a photomask for use in manufacturing integrated circuits.
Figure 2:
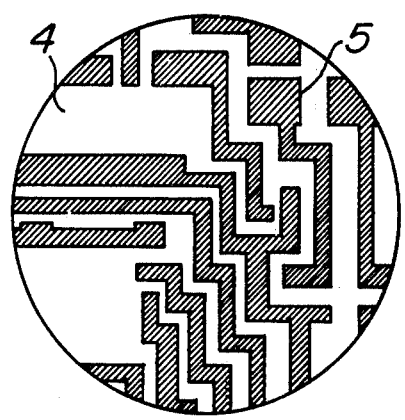
FIG. 2 is a microscopic image of a part of a photomask which does not include any defect.

In the embodiment shown in FIG. 6 the two patterns 20A and 20B of the same mask 20 to be checked are compared with each other. This is based on the fact that the mask has a number of identical patterns and a probability that the same defects are existent at identical portions of these patterns is negligibly small, and thus the defects can be detected very accurately without using the sample mask having the perfect patterns. In this method the number of the comparisons of the patterns situated near the peripheral portion of the mask is small and the detection accuracy for these peripheral patterns might be reduced. However, in practice only the patterns in the mask which are enclosed by a dotted circle 43 in FIG. 1 are used in manufacturing the semiconductor integrated circuits, and the peripheral patterns are not used. Thus there is arisen no serious problem.

In the above embodiment the signal representing the pattern 20B (FIG. 8d) is subtracted from the signal representing the pattern 20A (FIG. 8c). In addition to this the latter signal of FIG. 8c may be subtracted from the former signal of FIG. 8d so as to produce pulse signals having the opposite polarity to that shown in FIG. 8e. These two pulse signals are supplied to a rectifying circuit to produce a pulse signal having, for example a positive polarity. When such a pulse signal is supplied to the monitor 42, the defects are displayed as white images on the monitor screen. Instead of such measure the pulse signal of FIG. 8e may be supplied to a full-wave rectifying circuit.

In the explanation hereinbefore it is assumed that the defects have relatively large areas and should be detected as true defects. In the practical defect detection process, there are produced a number of very small defects in the vicinity of contours of the patterns due to the registration error and minute defects in these patterns which are not harmful for manufacturing the integrated circuits. It is quite undesirable that these small defects are detected as true defects. These small defects should be discarded as pseudo- or false-defects.

Figure 9:
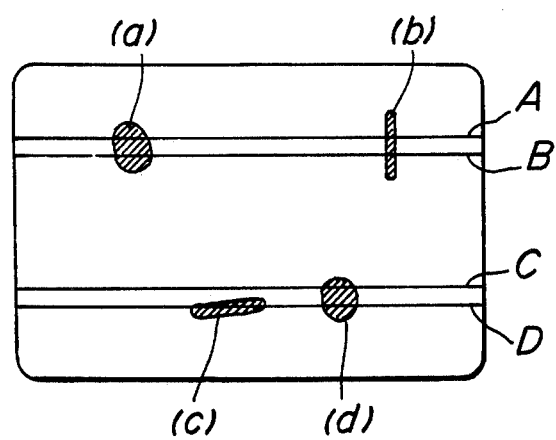
FIG. 9 is a schematic view of a monitor screen for illustrating various kinds of defects.

FIG. 9 illustrates four kinds of defects displayed on the monitor screen. The defects (a) and (d) should be identified as true defects, but the defects (b) and (c) should be discarded as pseudo-defects.

The present invention is to remove such pseudo-defects that are produced at the pattern contours mainly due to the registration error by decreasing a defect detection sensitivity in the vicinity of the pattern contours.

Figure 10A:
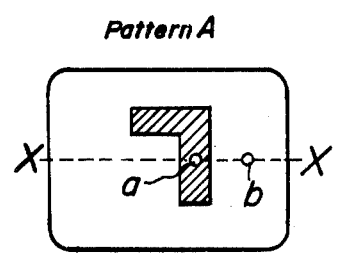
FIGS. 10a and 10b are schematic views of the monitor screen for showing two patterns to be compared with each other.
Figure 10B:
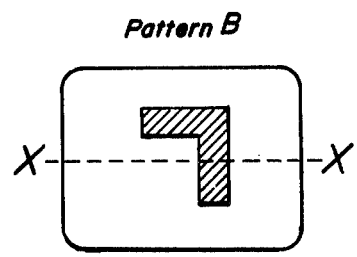

FIGS. 10a and 10b illustrate identical portions of two patterns A and B to be compared with each other. In the pattern A there are two defects a and b, but the other pattern B does not include a defect.

FIGS. 12a and 12b are waveforms of picture signals which are obtained by simultaneously scanning the patterns A and B along scanning lines X—X as shown in FIGS. 10a and 10b. The picture signal from the pattern A includes two defect signals a and b.

FIG. 11 is a circuit diagram illustrating an embodiment of a signal processing circuit of the defect detecting apparatus according to the invention in which the optically scanning device shown in FIG. 6 is employed. An output picture signal from the photomultiplier 31 which receives a light ray passing through the pattern A and an output picture signal from the other photomultiplier 32 which receives a light ray passing through the pattern B are supplied to a vertical contour signal producing section 50. This section 50 comprises a pair of one line delay circuits 51A and 51B and a pair of two line delay circuits 52A and 52B. As explained hereinafter a contour signal is formed with using one line delayed picture signals as standard signals and thus the one line delayed picture signals from the one line delay circuits 51A and 51B are supplied to a horizontal contour signal producing section 60.

At first the construction and operation of the horizontal contour signal producing section 60 will be explained. For the sake of explanation it is assumed that the picture signals shown in FIGS. 12a and 12b are one line delayed signals $A_1$ and $B_1$ which have passed through the one line delay circuits 51A and 51B, respectively. In the horizontal contour signal producing section 60 there are provided a pair of first delay circuits 61A and 61B having a delay time of 0.2 $\mu$s and a pair of second delay circuits 62A and 62B having a delay time of 0.4 $\mu$s. At the outputs of the first and second delay circuits 61A and 62A are produced delayed signals $A_2$ and $A_3$ shown in FIGS. 12c and 12e, respectively. The delay times of 0.2 $\mu$s and 0.4 $\mu$s correspond substantially to lengths of 1 μm and 2 μm, respectively measured on the pattern. This means that the length of the horizontal scanning is equal to 250 μm and the light spot scans along this length for about 40 μs. FIGS. 12d and 12f show delayed signals $B_2$ and $B_3$ obtained at outputs of the delay circuits 61B and 62B.

There is further provided first and second AND gates 63A and 65A. The picture signal $A_3$ from the second delay circuit 62A and the non-delayed picture signal $A_1$ after being inverted in phase by an inverter 64A are supplied to the first AND gate 63A to produce a signal $A_4$ shown in FIG. 12g. To the second AND gate 65A are supplied the non-delayed signal $A_1$ and the delayed signal $A_3$ after being inverted in phase by an inverter 66A to produce a signal $A_5$ illustrated in FIG. 12i. These signals $A_4$ and $A_5$ are supplied to an OR gate 67A to produce a signal $A_6$ shown in FIG. 12k. This signal $A_6$ represents a contour region along the contour of the pattern A and this contour region has a width of about 2 μm corresponding to 0.4 μs.

As to the picture signal related to the other pattern B the same treatment is effected by providing third and fourth AND gates 63B and 65B and inverters 64B and 66B to obtain signals $B_4$ and $B_5$ shown in FIGS. 12h and 12j, respectively and then these signals $B_4$ and $B_5$ are supplied to an OR gate 67B to produce a signal $B_6$ illustrated in FIG. 12l. This signal $B_6$ represents a contour region which situates in the vicinity of the contour of the other pattern B and has a width of about 2 μm.

As explained above the signals $A_6$ and $B_6$ represent the contour regions of the patterns A and B, respectively and have the width of 1 μm in the horizontal direction at both sides of the boundary of the patterns. It is possible to use a logic sum of these signals $A_6$ and $B_6$ as a horizontal contour signal. However if the two patterns to be compared with each other are relatively deviated in the horizontal direction, the width of the horizontal contour signal is increased and defects near the contours might not be correctly detected. Moreover the large deviation could not be also detected. For example, if the two patterns A and B are shifted in the horizontal direction relative to each other by 1 μm, the width of the contour signal corresponds to a length of 3 μm and thus any defects in this contour region could not be detected. In order to avoid such a drawback in the present embodiment the superimposed region of the signals A and B is extracted as the contour signal. To this end the signals $A_6$ and $B_6$ supplied from the OR gates 67A and 67B, respectively are fed to an AND gate 68 to obtain a signal $AB_7$ shown in FIG. 12m and this signal is used as a horizontal contour signal.

Next the construction and operation of the vertical contour signal producing section 50 will be explained. The section 50 comprises two-line delay circuits 52A and 52B as well as the one-line delay circuits 51A and 51B. As explained above with reference to the horizontal contour signal producing section 60 the non-delayed signal and two-line delayed signal are processed by AND gates 53A, 53B, 55A, 55B and 58; inverters 54A, 54B, 56A and 56B; and OR gates 57A and 57B to produce a vertical contour signal from the AND gate 58. This contour signal $AB_8$ represents a superimposed contour region which has a width of one line pitch in the vertical direction at both sides of the contour.

As explained above in the horizontal contour signal generating section 60 the signals $A_2$ and $B_2$ delayed by 0.2 μs are used as the standard signals and these delayed signals are also used as standard signals in a defect detecting section 70 so as to generate a defect signal. In the defect detecting section 70 the signal $A_2$ related to the pattern A is supplied to first slicer circuits 71A and 72A having white and black slice levels which are set near the white and black levels of the picture signal, respectively. The signal $B_2$ is supplied to second slicer circuits 71B and 72B with white and black slicing levels closely set to the white and black levels of the picture signal.

FIGS. 13a to 13f are waveforms showing an operation of the slicer circuits. In general the defects are small and its level does not greatly differ from the black or white level. For example the defect a in the pattern A of FIG. 10a is a defect in the deposited film i.e. opaque portion and the defect b in the pattern B is a residual portion of the deposited film and both defects a and b are very small. Therefore the signal $A_2$ obtained by scanning the pattern A along the line X—X is as shown in FIG. 13a and the defect signal portions a and b deviate from the black and white levels, respectively only slightly. Thus if the picture signal were sliced by an intermediate or middle level between the black and white levels, these defects a and b could not be detected at all. In the present embodiment the black and white slicing levels are set very near the black and white levels, respectively of the picture signal so as to detect the small defects with a high sensitivity. Therefore from the first white and black slicer circuits 71A and 72A are derived the signals illustrated in FIGS. 13c and 13e, respectively. In these signals the defects a and b are effectively detected. The signal $B_2$ which is obtained by scanning the pattern B along the line X—X is processed by the second white and black slicer circuits 71B and 72B so as to produce the signals shown in FIGS. 13d and 13f, respectively.

The output signals from the first and second white slicer circuits 71A and 71B are supplied to a first differential amplifier 73 to produce a signal shown in FIG. 13g. The output signals from the first and second black slicer circuits 72A and 72B are supplied to a second differential amplifier 74 to obtain a signal illustrated in FIG. 13h. Now it is assumed that the patterns A and B are slightly shifted in the horizontal direction by for example 0.5 μm, there are produced pseudo-defects q at the contour region as well as the true defects a and b in the output signals of FIGS. 13g and 13h. Then these output signals are suitably processed by first and second circuits 75 and 76, respectively to produce output signals shown in FIGS. 13i and 13j, respectively. These output signals are supplied to an OR gate 77 to produce a signal of FIG. 13k. This signal includes the pseudo-defect signals q as well as the true defect signals a and b.

As illustrated in FIG. 11 the output signal from the defect detecting section 70 is supplied to a control section 80. The section comprises an OR gate 81 which receives the vertical and horizontal contour signals from the sections 50 and 60, respectively and produces an output contour signal shown in FIG. 13l. The section 80 further comprises a gate circuit 82 which is controlled by the contour signal from the OR gate 81 in such a manner that the gate is closed during the occurrence of the contour signal g, so as to prevent the passage of the pseudo-defect signals q therethrough. In this manner the pseudo-defect signals q in the signal shown in FIG. 13k are removed and only the true defect signals a and b are supplied to an output terminal 83 as an output defect signal.

Figure 15:
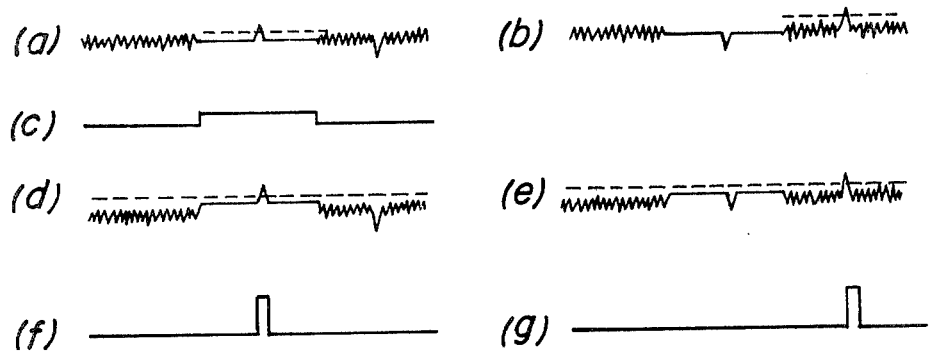
FIGS. 15a to 15g are waveforms for explaining the operation of the circuit of FIG. 14.

FIG. 14 is a block diagram showing another embodiment of the pattern defect detecting apparatus according to the invention. The present embodiment differs from the previous embodiment shown in FIG. 11 only in the construction and operation of the defect detecting section. The defect detecting section 90 of this embodiment comprises a differential amplifier 91 to which are supplied the signals $A_2$ and $B_2$ from the first and second 0.2 μs delay circuits 61A ad 61B, respectively of the horizontal contour signal producing section 60. An output signal from the differential amplifier 91 is shown in FIG. 15a. This output signal is directly supplied to a first mixer 92 and is also supplied to a second mixer 94 through an inverter 93. An output signal from the inverter 93 is illustrated in FIG. 15b. As can be seen from FIGS. 15a and 15b the signal obtained by scanning the transparent portion of the pattern includes large noise, but the signal corresponding to the opaque portion of pattern does not include large noise. This is due to characteristics of an active surface of the photomultipliers 31 and 32. Therefore if the signal of FIG. 15a is sliced by a level which is slightly higher than the black level as shown by a broken line, there is a greater chance that noises included in the signal corresponding to the transparent portion of pattern are also detected as defects. On the other hand if the slicing level is set to a level which is substantially higher than the black level, the small defects might not be detected. According to the present embodiment the small defects can be detected by increasing the signal level at the opaque portion of pattern, because the picture signal corresponding to the opaque portion does not include large noise. For this purpose to the first and second mixers 92 and 94 is supplied a signal shown in FIG. 15c which is obtained by supplying the signals $A_2$ and $B_2$ to an OR gate 97 through inverters 95 and 96, respectively. In the mixers 92 and 94 this signal is mixed at a suitable level with the signals supplied from the differential amplifier 91 to produce signals shown in FIGS. 15d and 15e, respectively. These signals are fed to black and white slicer circuits 98 and 99, respectively, in which the signals are sliced with slicing levels shown by broken lines to produce signals illustrated in FIGS. 15f and 15g, respectively. These signals include not only the true defect signal, but also the pseudo-defect signal. The pseudo-defect signal can be removed by supplying these signals to the control section 80 through an OR gate 100 in the same manner as explained above. In this manner at the output terminal 83 there can be obtained the defect signal from which the pseudo-defect signals have been removed and true defects have been detected with a high sensitivity.

Figure 16:
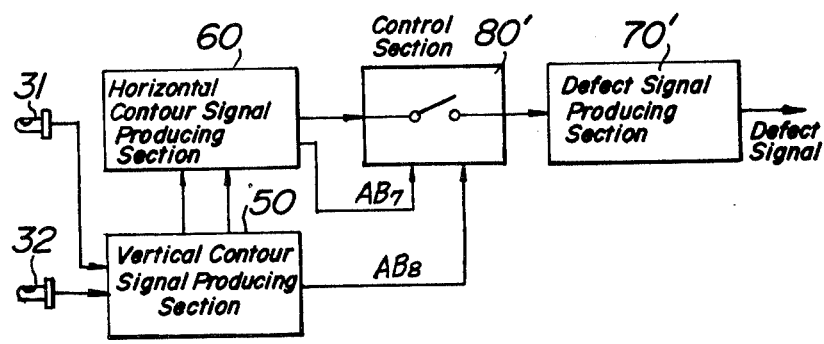
FIGS. 16, 17 and 18 are block diagrams showing another embodiments of the signal processing circuit of the defect detecting apparatus according to the invention.

FIG. 16 is a block diagram showing another embodiment of the defect detecting apparatus according to the invention. In the present embodiment the vertical and horizontal contour signals $AB_8$ and $AB_7$ supplied from the vertical and horizontal contour signal producing sections 50 and 60 are fed to a control section 80′ comprising an electronic on-off switch. To the control section 80′ is also supplied the picture signal from the 0.2 μs delay circuit 61A of the horizontal contour signal producing section 60. The electronic switch of the control section 80′ is so controlled by the contour signals that the picture signal is supplied to a defect decision section 70′ only when the contour signals $AB_7$ and $AB_8$ are not fed to the control section 80′. The defect detecting section 70′ can have a very high sensitivity for defect detection.

Figure 17:
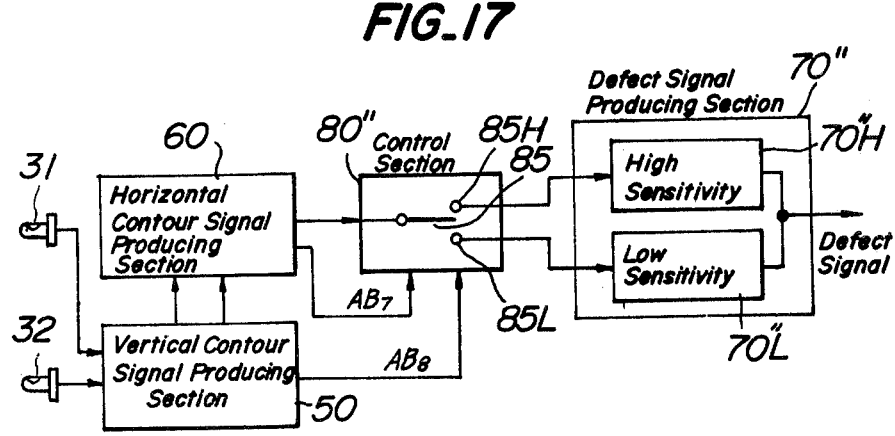

FIG. 17 is a block diagram illustrating still another embodiment of the defect detecting apparatus according to the invention. In this embodiment the vertical and horizontal contour signals $AB_8$ and $AB_7$ from the vertical and horizontal contour signal producing sections 50 and 60, respectively are supplied to a control section 80″ comprising an electronic changeover switch 85. To the section 80″ is also supplied the picture signal from the horizontal contour signal producing section 60. When the contour signals are not fed to the section 80″, the picture signal is supplied through a contact 85H of the switch 85 to a high sensitivity defect detector 70″H provided in a defect detecting section 70″ which can detect the defects with a very high sensitivity. Whilst when the contour signals are supplied to the control section 80″, the picture signal is fed through a contact 85L of the switch 85 to a low sensitivity defect detector 70″L which detects the defects with a lower sensitivity. According to this embodiment the defects in the contour region are detected at the lower sensitivity and thus true defects of large dimensions in the contour region are effectively detected. The defect detection sensitivity can be adjusted in various manners. For example this can be effected by changing the slicing levels of the black and white slicer circuits provided in the defect detecting section; which is indicated in the drawing as variable resistors.

In the embodiments explained above the contour signals are formed from the non-delayed signal and two-line or 0.4 μs delayed signals, but in case of forming the horizontal contour signal the non-delayed and 0.2 μs delayed signals and the 0.2 μs and 0.4 μs delayed signals, respectively are compared with each other and the difference signals may be combined by means of an OR gate. In this case the number of circuit elements is somewhat increased, but there is formed no serration denoted by a reference S in FIG. 12k.

The slicer circuits 71A, 71B, 72A and 72B provided in the defect detecting section 70 in FIG. 11 may be provided at inputs of the contour signal producing sections 50 and 60. In this case when use is made of a digital delay circuit, a single picture element can be treated by a single bit (the picture signal is represented by either white or black) and thus the construction of the delay circuit becomes simpler. It should be noted that in such a case there will be formed four images from which the contour signal will be produced and thus the number of circuit elements will be increased accordingly. However by means of adopting the following measure the number of circuit elements can be materially decreased.

Figure 18:
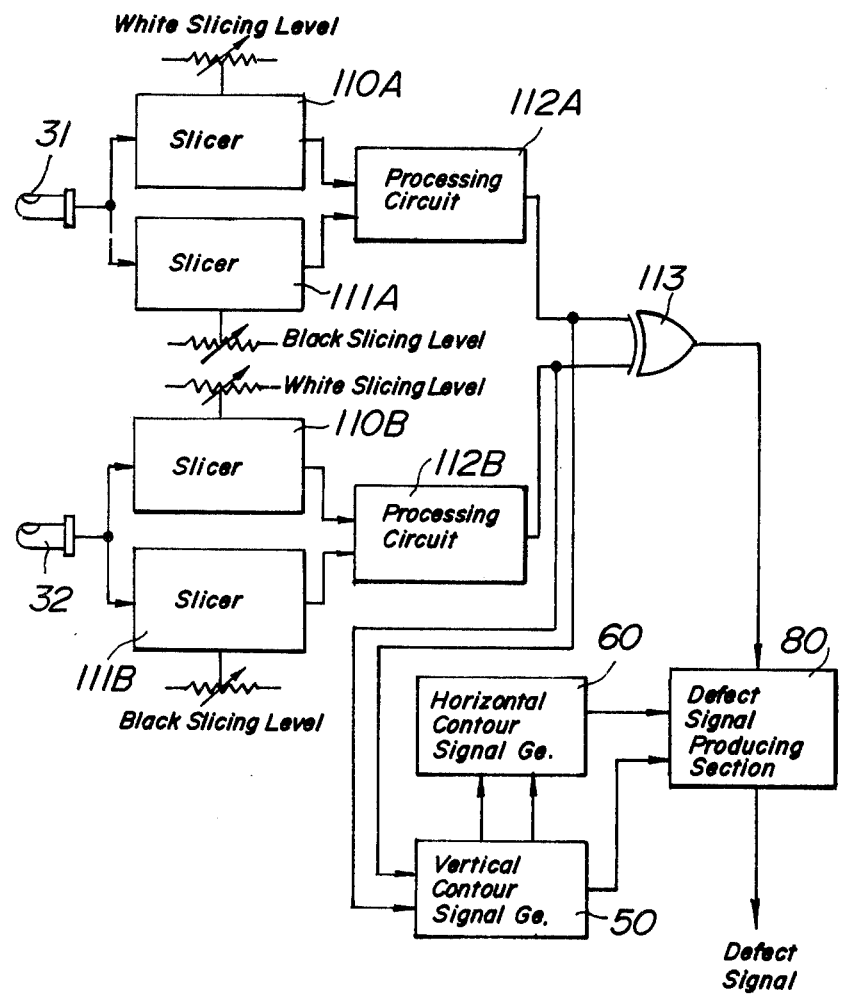
Figure 19:
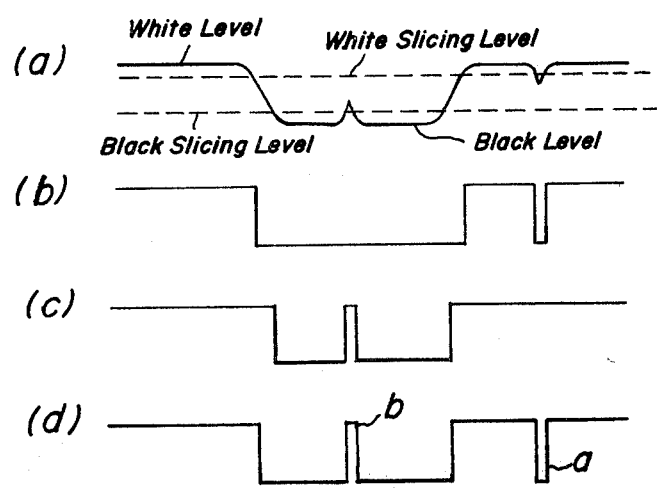
FIGS. 19a to 19d are waveforms for explaining the operation of the circuit of FIG. 18.

FIG. 18 is a block diagram showing still another embodiment of the defect detecting apparatus according to the invention and FIGS. 19a to 19d illustrate waveforms for explaining the operation thereof. In the present embodiment the output picture signal from the photomultiplier 31 corresponding to the pattern A is supplied to a white slicer circuit 110A and a black slicer circuit 111A. As shown in FIG. 19a in these slicer circuits the picture signals are sliced with white and black slicing levels, respectively which are set near the white and black levels, respectively to produce signals shown in FIGS. 19b and 19c, respectively. Similarly the picture signal from the photomultiplier 32 corresponding to the pattern B is sliced in white and black slicer circuits 110B and 111B to produce signals which are similar to those shown in FIGS. 19b and 19c, respectively. These signals are supplied to processing circuits 112A and 112B comprising flip-flops having priority order to produce signals shown in FIG. 19d. These signals contain a black defect a in the transparent portion of the pattern and a white defect b in the opaque portion. These signals are supplied to the vertical and horizontal contour signal producing sections 50 and 60 to form the vertical and horizontal contour signals, respectively in the manner explained above. The output signals from the processing circuits 112A and 112B are fed to a defect detecting section 113 comprising an exclusive OR gate to produce the defect signal which includes pseudo-defect signals as well as true defect signals. This defect signal is supplied to a control section 80. As explained above to the control section 80 is supplied the contour signal as a control signal so as to remove the pseudo-defect signals from the output defect signal. In this manner the defect signal including the detected true defects can be derived from the control section 80. In the present embodiment since the signal is processed after the bivalent signal including both the black and white defects has been formed, the construction becomes simple as compared with the previously explained embodiment. Moreover the contour signal is produced from this bivalent signal and thus the single picture element can be processed by the single bit so that the digital delay circuits can be also simply constructed.

Figure 20:
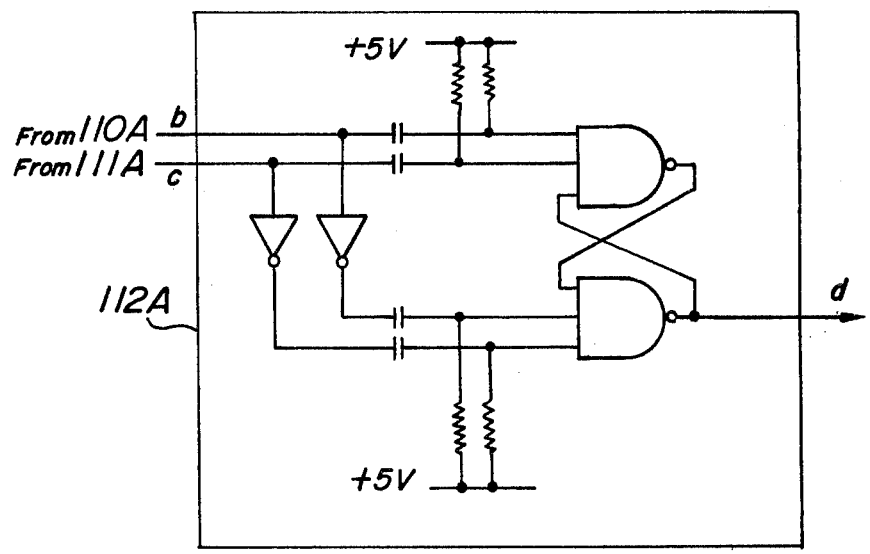
FIG. 20 is a circuit diagram of a portion of the circuit shown in FIG. 18.

FIG. 20 is a circuit diagram showing an embodiment of the signal processing circuit 112A. When the two input signals b and c from the slicer circuits 110A and 111A fall successively, the output signal d falls in synchronism with the signal b or c which falls formerly and when the signals b and c rise in succession, the output signal d rises in synchronism with the formerly rising signal b or c. That is to say the circuit of FIG. 20 operates as a flip-flop having the priority succession.

As explained above according to the invention the true defects can be detected with the high sensitivity while removing the pseudo-defects which appear in the vicinity of the contours of the patterns. The defect signal thus obtained can be further processed in various manners. One embodiment of the processing steps will be explained hereinafter.

Figure 21:
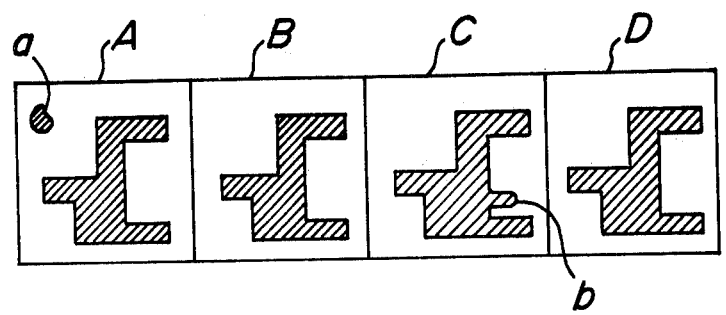
FIG. 21 is a plan view depicting a series of patterns including defects.

According to the present invention it is further posible to identify which pattern A or B includes the detected defects. The basic operational principle of this identification will now be explained with reference to FIG. 21. It is assumed that four patterns A, B, C and D are successively compared to detect defects. In this case the patterns A and C include defects a and b, respectively. In a first comparison of the patterns A and B the defect a is detected, but at this time it is impossible to determine which pattern A or B includes this detected defect a. In a second comparison between the patterns B and C there is no defect at a related position at which the defect a has been detected. Then it is decided that the detected defect a is included in the pattern A. During this second comparison a new defect b is detected at a different position. However at this time it cannot be certained which pattern B or C includes this detected defect b. This defect b is also detected in a third comparison between the patterns C and D. Then it is determined that the defect b is included in the pattern C. That is to say when a defect is detected in a comparison, a position of this detected defect is stored and if a defect is detected in a next comparison at the same position, it is certified that the detected defect is included in the pattern which has been commonly used in the above two successive comparisons. This principle of identifying the defect is based on the fact that a probability of existing defects in successively compared patterns at the same position is very small.

Figure 22:
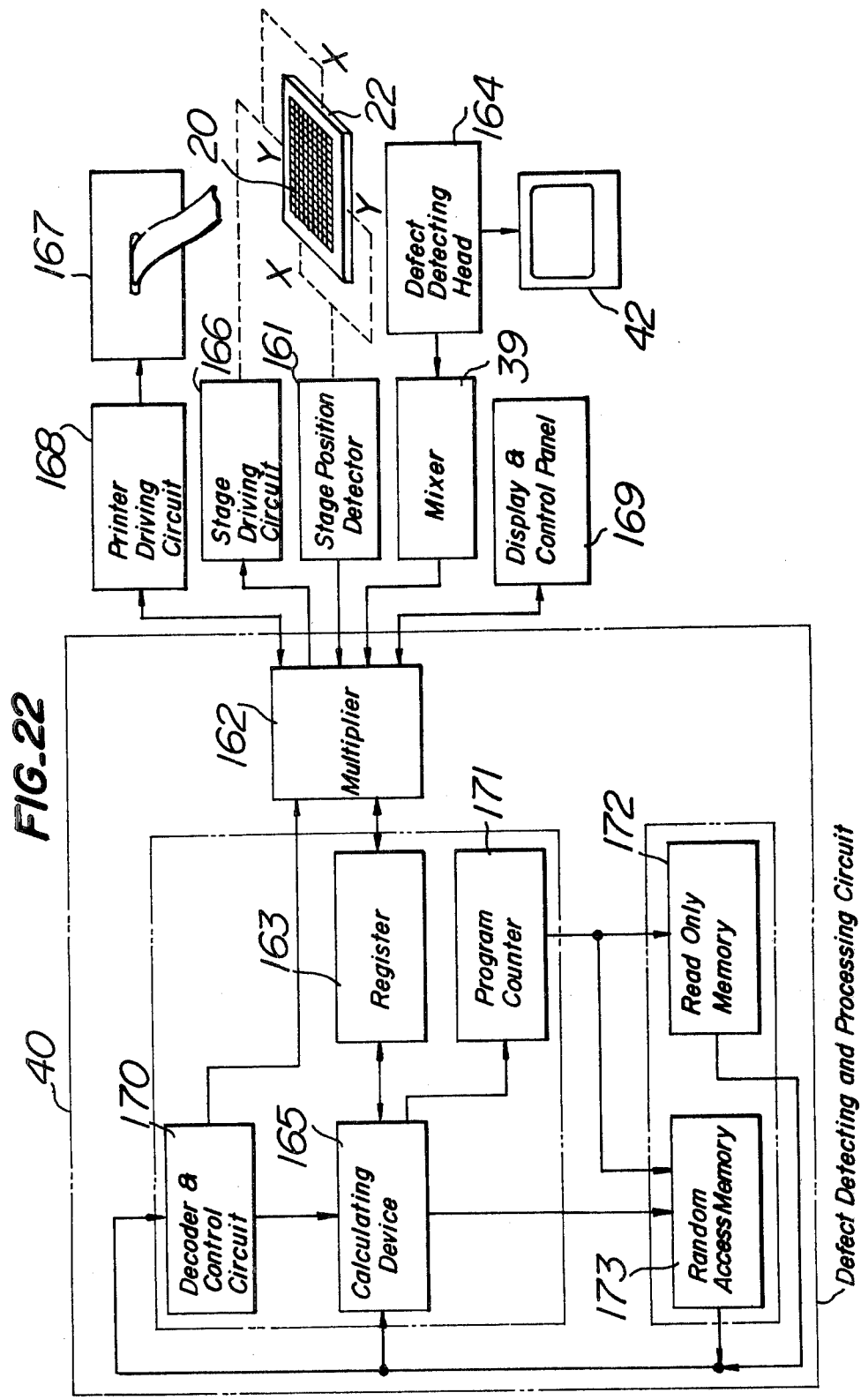
FIG. 22 is a block diagram showing the whole construction of an embodiment of the defect detecting apparatus according to the invention.

FIG. 22 is a block diagram showing an embodiment of the defect detecting and processing circuit 40 (see FIG. 7). In the present embodiment use is made of the scanning apparatus shown in FIG. 6 and the mask 20 to be checked is placed on the carrier stage 22. Two patterns 20A and 20B in this mask are to be compared with each other. As illustrated in FIG. 22 there is provided a stage position detecting device 161 which supplies a signal representing coordinates of the stage 22. This signal is supplied to a resistor 163 through a multiplier 162. There is further provided a defect detecting head 164 comprising the first and second photoelectric converters 31 and 32 and output signals from this head 164 are supplied through the slicer 39 and the multiplier 162 to the register 163. This register 163 operates as a buffer register and temporarily stores data between the multiplier 162 and an operating or calculating device 165. To the multiplier 162 are connected a stage driving circuit 166, a printer 167, a printer driving circuit 168 and a display and control panel 169 by means of which a user can preset various kinds of defect detecting operations.

There are further provided an order decoder and control circuit 170 for controlling the operation of the calculating device 165 and the multiplier 162, a program counter 171 for counting a program address from the calculating device 165, a read only memory 172 for storing contents of programs and a random access memory 173 for storing data from the calculating device 165.

Figure 23:
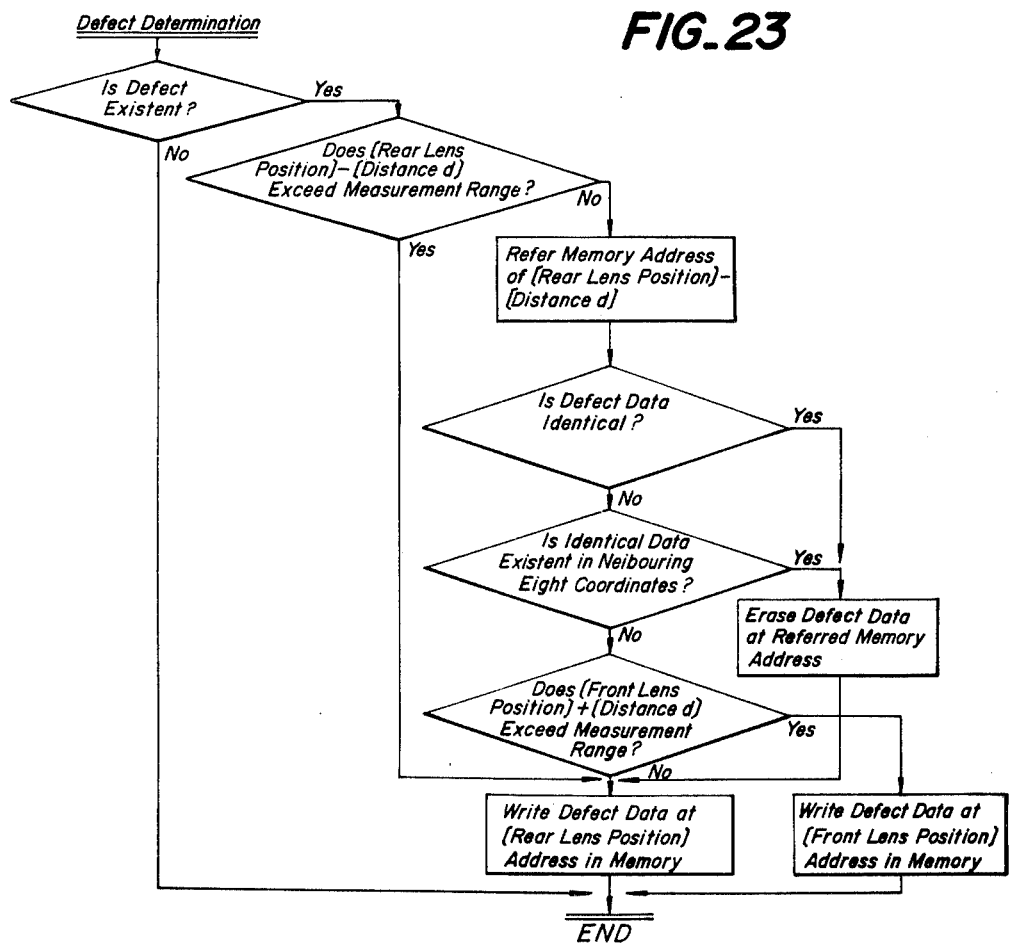
FIG. 23 is a flow chart illustrating the operation of the apparatus of FIG. 22.

Now the operation of the defect detecting and processing circuit 40 will be explained with reference to a flow chart shown in FIG. 23. The circuit 40 can effect various operations. An operation for determining which pattern includes a detected defect will be first explained. It is assumed that a mask used for manufacturing integrated circuits includes 13×13 chips and each chip is of a rectangular shape having dimension of 5 mm×5 mm. In the defect detecting head 164 a single chip is divided into a number of regions of 250μ×250μ and each region is displayed on the screen of the monitor 42. The single region is further divided into 25 domains each having a dimension of 50μ×50μ. Therefore in the single chip there are 10,000 domains (100 domains in the horizontal direction and 100 domains in the vertical direction). The stage position detecting device 161 must express each region of a respective chip as X, Y coordinates and the stage driving circuit has to denote each region of a respective chip. Each of 25 domains in a respective region is denoted by a deflection signal for the flying spot cathode ray tube 23 shown in FIG. 6. That is to say each of the horizontal and vertical deflection signals is divided into five portions and these signal portions are used as domain denoting signals. In this manner each of 10,000 domains in a respective chip are provided with X and Y coordinates which can be handled in the circuit 40. The stage position detecting device 161 produces such X and Y coordinates.

Before the measurement a distance d between the optical axes of the lenses 27 and 30 is set by means of the display and control panel 169. For example, if two adjacent chips are to be compared with each other, the distance d must be set to 5 mm and if every other chips are to be compared with each other, the distance d has to be set to 10 mm. This setting operation may be carried out by means of a preset counter. The set value of the distance d is supplied from the panel 169 to the defect detecting and processing circuit 40. In order to adjust the actual distance between the optical axes to the set value the adjusting mechanisms 33 and 34 shown in FIG. 6 are handled with viewing screen of the monitor 42 which displays two pattern images so as to registrate these two images. In the present example the distance d is set to 10 mm.

Figure 24A:
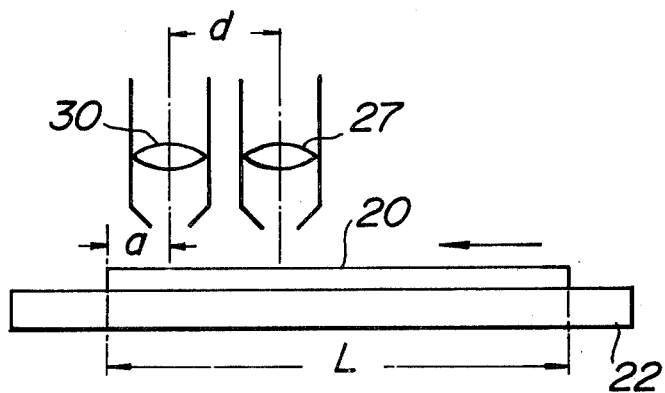
FIGS. 24a to 24c are schematic views showing relative arrangement of the mask and a pair of lenses.
Figure 24B:
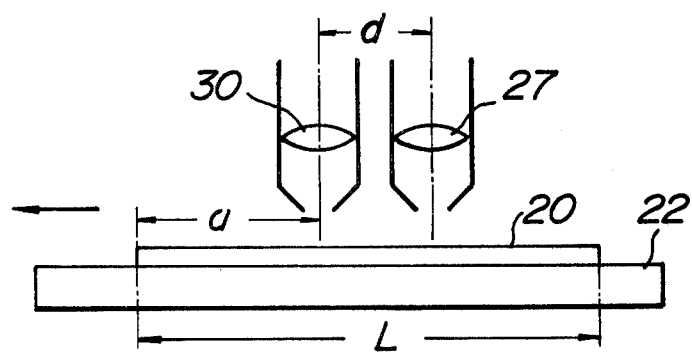
Figure 24C:
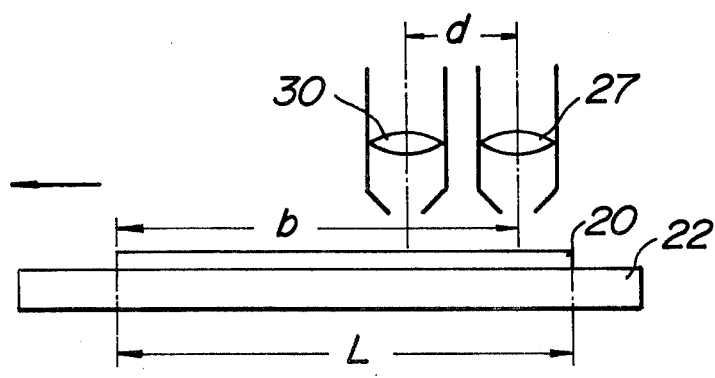

In case of determining which pattern includes the detected defect it is necessary to consider separately the case in which both of two chips to be compared do not situate at a periphery of the mask and the case in which at least one of the two chips situates at the periphery of the mask. FIG. 24 illustrates this situation. In FIG. 24 the stage 22 is to be moved into the left hand as shown by an arrow. Thus the lens 27 is termed as a front lens and the lens 30 as a rear lens. A length of the mask 20 is denoted by L which will be called as a measurement range. In the above example in which the mask has 13×13 chips each having the dimension of 5 mm×5 mm, the measurement range L amounts to 65 mm. Each chip is represented by 100×100 X, Y coordinates and thus the whole mask is expressed by 1,300×X, Y coordinates. Now it is assumed that a left hand end of the measurement range L is expressed as a coordinate "0" and a right hand end is expressed as a coordinate "1,300". FIG. 24a illustrates a situation in which a distance a between the optical axis of the rear lens 30 and the left hand end of the measurement range L is smaller than the distance d, FIG. 24b shows a situation in which the distance a is longer than the distance d and FIG. 24c depicts a situation in which a sum of a distance b between the optical axis of the front lens 27 and the left hand end of the measurement range and of the distance d is longer than the range L. Therefore in the situation of FIG. 24a a coordinate which is obtained by subtracting the distance d from a coordinate of the optical axis position of the rear lens 30 is far leftward than the left hand edge of the range L and becomes a negative value. In the situation of FIG. 24c a coordinate of the sum of a coordinate of the optical axis of the front lens 27 and the distance d is far rightward than the right hand edge of the range L and becomes a larger value than "1,300".

From the defect detecting head 164 is supplied a signal which represents existence or non-existence of a defect to the defect detecting and processing circuit 40. At the same time from the stage position detecting device 161 the coordinates of the chip being checked is supplied through the register 163 to the calculating device 165. As shown in the flow chart of FIG. 23 the existence or non-existence of defect is first determined. If no defect is detected, the process for this coordinates' position has been completed and the calculating device 165 signals the program counter 171 so as to start a new program cycle. If a defect is detected, the calculating device 165 supplies a signal to the program counter 171 which drives the read only memory 172 so as to read out a program which effects a determination whether a distance=[position of rear lens]−[distance d] exceeds the measurement range or not. When it is determined that the above mentioned distance exceeds the measurement range, data for representing that the defect is included at the coordinates of the detected position by the rear lens 30 is stored in the random access memory 173. This program cycle has been ended by this storing process and a similar process is started for a new checking position.

On the contrary when it is determined that the distance of [rear lens position]−[distance d] does not exceed the measurement range, the program is further continued and a coordinate of [rear lens position]−[distance d] is calculated. Then it is determined whether or not data for expressing that the defect is existent at the calculated coordinate position is stored in the random access memory 173. As the result of this determination if the defect data has been stored at the related position, this defect data in the memory 173 is erased and data indicating that the defect is existent at the coordinate of the rear lens position is newly stored in the memory 173. By this storing procedure this program cycle has been completed and a new program cycle is started.

On the contrary if it is determined that the defect data is not sotred at the corresponding coordinate position of [rear lens position]−[distance d], it is further determined whether or not a defect data is stored in eight neighbouring domains. By this process if it is determined that the defect data is stored in any one of these domains, the defect data stored at the related position is erased and data expressing that the defect is existent at the coordinate position of the rear lens is newly stored in the random access memory 173. This program cycle has been completed by this storing process.

If it is determined that none of the eight neighbouring domains includes a defect data, it is further checked whether or not a distance=[front lens position]+[distance d] exceeds the measurement range. As the result of this checking if said distance does not exceed the measurement range, the defect data is stored at the coordinate position of the rear lens position and the program cycle has been ended.

On the contrary if it is certified that said distance=[front lens position]+[distance d] exceeds the measurement range, data expressing that there is a defect at the coordinate position of the front lens is newly stored in the random access memory 173.

The above program cycles are carried out repeatedly and the defects, coordinates in the relevant chip of the mask 20 can be successively stored in the random access memory 173.

As explained above the defect detecting and processing circuit 40 shown in FIG. 22 can effect various operations with utilizing the information data stored in the above mentioned manner. Next these operations will be explained.

TYPING OUT THE NUMBER OF DEFECTS

By operating a button on the control panel 169 the number of defects in each chip is typed out. This is effected by counting the number of defects in each chip stored in the random access memory 173 and supplying this count value to the printer driving circuit 168 through the register 163 and multiplier 162. The driving circuit 168 drives the printer 167 to print out the number of defects.

DISPLAY OF OVERLOW OF THE NUMBER OF DEFECTS

As described above in the random access memory 173 the defect data for each chip is stored. If a chip has a number of defects, this chip will be determined as an inferior one. Therefore it is neither necessary nor preferable to store the data of such a number of defects. For example five defects at most can be sotred for a single chip and if defects more than five are detected, the defect data is not stored any more. By such a measure the capacity of the memory may be reduced. Upon typing out the defect data such a chip is represented as "overflow".

SKIP SCANNING FOR INFERIOR CHIP

As described above if a chip has more than five defects, this chip is identified as an inferior one. If this overlow is detected during the check period, it is not necessary to check this chip further more. In this case the scanning is skipped to a next chip. By this skipping operation the whole checking time may be reduced.

DISPLAY OF DEFECT ON MONITOR SCREEN

Since the coordinates of the detected defects have been stored in the memory 173, an image of the pattern portion including the defect can be automatically displayed on the screen of the monitor 42 by reading out the coordinates of the related defect and supplying the read out coordinates to the stage driving circuit 166. As explained above this display is effected for each region of the dimension $250\mu \times 250\mu$. Moreover it is possible to denote the particular section which will be displayed on the monitor screen under the control of the panel 169.

By displaying the image of the defect on the monitor, it is possible to check in detail condition and kind of the defects. For example if a dirt applied on the mask has been detected as a mask defect, this dirt is investigated in detail and can be removed. In actual apparatus it is important to check each defect separately in this manner.

TYPING OUT THE NUMBER OF DEFECTS FOR EACH ROW OF CHIPS

As explained above the mask has regular array of chips, i.e. thirteen chips are arranged along each horizontal row. For example, after thirteen chips in the same row have been checked, the number of detected defects can be typed out for each chip and if overflows are detected for more than four chips, the mask is identified as an inferior one and further checking operation for this mask can be deleted. In this manner the checking efficiency may be increased materially.

Figure 25:
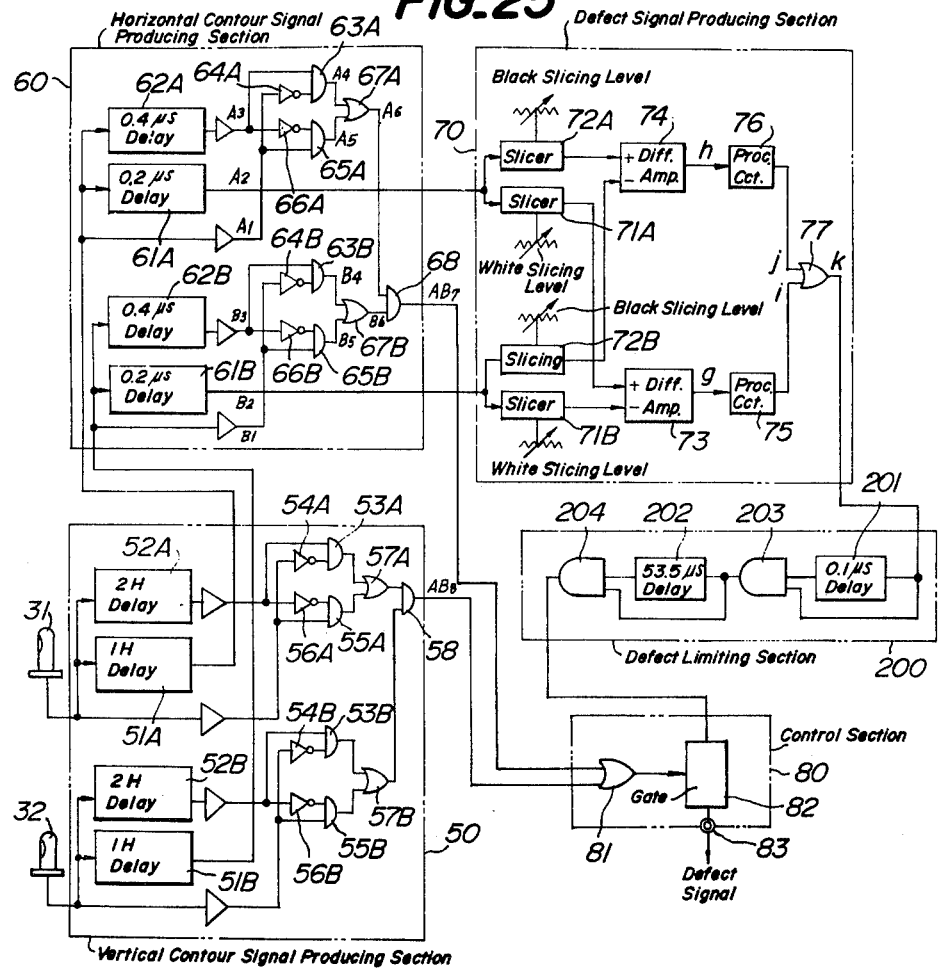
FIG. 25 is a block diagram showing still another embodiment of the processing circuit of the defect detecting apparatus according to the invention.

FIG. 25 is a block diagram showing still another embodiment of the invention which is similar to that illustrated in FIG. 11 except that there is connected between the defect detecting section 70 and control section a defect limiting section 200 comprising first and second delay circuits 201 and 202 and first and second AND gates 203 and 204. The output signal from the defect detecting section 70 is supplied through the first delay circuit 201 having a delay time of about 0.1 $\mu$s to one input of the first AND gate 203. To the other input of this AND gate is supplied directly the signal. An output signal from the first AND gate 203 is supplied through the second delay circuit 202 having a delay time of one line period, i.e. 53.3 $\mu$s to one input of the second AND gate 204, to the other input of which is supplied directly the output signal from the first AND gate 203. An output signal of the second AND gate 204 is supplied to the gate 82 of the control section 80.

Figure 26:
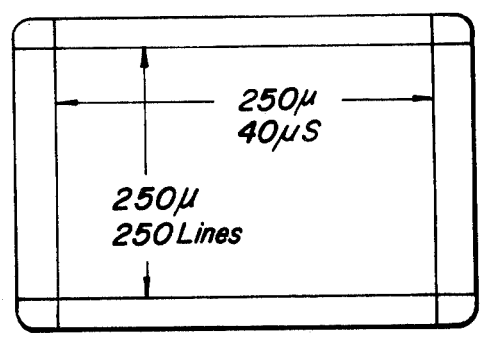
FIG. 26 is a plan view showing diagrammatically a scanning raster.

The reason for selecting the delay times of the first and second delay circuits 201 and 202 to 0.1 $\mu$s and 53.3 $\mu$s, respectively is as follows. The raster scanning system of the present flying spot scanner is set as follows. The number of scanning lines per field is 625 lines, adapting 2:1 interlace and the number of fields per second is 60. FIG. 26 shows diagrammatically a raster thus formed. As shown in FIG. 26 a length of 250 $\mu$m in the horizontal direction corresponds to a time period of 50 $\mu$s and a length of 250 $\mu$m in the vertical direction corresponds to 250 scanning lines. That is to say during the time period of 40 $\mu$s in the horizontal scanning period of 53.3 $\mu$s the portion of the mask having a length of 250 $\mu$m in the horizontal direction is picked-up and during 250 scanning line period in 312.5 scanning line period a portion of the mask having a length of 250 $\mu$m in the vertical direction is picked-up. A magnification of the lenses and the electron beam deflection is so determined that the above conditions can be satisfied. In the present embodiment the pseudo-defects appearing in regions other than the contour regions are to be rejected by deleting the small defects having dimensions smaller than one micron meter in the horizontal and vertical directions. Therefore in the horizontal direction any defect smaller than 1 $\mu$m corresponding to a time period of 0.08 $\mu$s are to be removed and in the vertical direction any small defects having dimensions smaller than 1 $\mu$m corresponding to one horizontal scanning period of 53.3 $\mu$s are to be removed. In accordance with the above mentioned calculation the delay time of the first delay circuit 201 is determined to 0.1 $\mu$s and that of the second delay circuit 202 is set to 53.3 $\mu$s.

By connecting the above explained defect limiting section 200 to the output of the defect detecting section 70 the pseudo-defects which are smaller in dimension than 1 $\mu$m in the vertical and/or horizontal direction can be removed from the output defect signal derived from the output terminal 83. In this case the defect limiting section 200 is considered to decrease the sensitivity, but by providing such a section 200 the white and black slicing levels at the slicer circuits 71A; 71B and 72A, 72B can be set further near to the white and black levels, respectively of the picture signal and thus the overall sensitivity of the defect detecting apparatus can be substantially increased. The setting of the white and black slicing levels nearer to the white and black levels, respectively is based on the fact that large noise does not almost appear at the same position.

The present invention is not limited to the embodiments mentioned above, but many modifications are possible within the scope of the invention. For example, in the above embodiment the flying spot scanner, the optical system and the photoelectric converters are fixedly arranged and the patterns are moved while placing it one the carrier stage. It is also possible to arrange the pattern fixedly and move the scanner, the optical system and the photo-electric converters. In the above embodiment the carrier stage may be moved in a stepwise manner instead of in a continuous manner. In the embodiments the photoelectric converters are arranged to receive the light spot passing through the patterns, but they may be arranged to receive the light spot reflected from the patterns. In the above embodiment use is made of the flying spot scanner tube as the device for producing the scanning light spot, but any other devices such as a device using a vibrating mirror may be utilized. Moreover in case of using a sample pattern without defect as one of two patterns to be compared with each other as shown in FIG. 5 the contour signal may be produced by the picture signal obtained by scanning the sample pattern.

Furthermore in the embodiment shown in FIG. 17, the change over switch 85 is provided at the input of the defect defecting section 70'', but it may be arranged at the output of the section 70''. In such a case the picture signals may be supplied in parallel to the first and second defect detectors 70''H and 70''L.

In the embodiments shown in FIGS. 11 and 14 the delay time of first and second delay circuits 52A and 52B in the vertical contour signal producing section 50 is set to twice of the line scanning period H and the delay time of the third and fourth delay circuits 52A and 52B is set to the horizontal line scanning period H. These delay times may be set to different values. However these delay times should be integer multiples of the horizontal scanning period H. Further the delay time of the third and fourth delay circuits is not always necessarily set to a half of the delay time of the first and second delay circuits, but should be shorter than the later delay time. Similarly the delay times of the delay circuits 61A, 61B, 62A and 62B may be set to different values than those explained above. In a case may be the delay time of the delay circuits 62A may be different from that of the delay circuit 62B. At any rate the delay time of the delay circuits 61A and 61B should be shorter than the delay time of the delay circuits 62A and 62B.

Further in the above embodiments there are provided the white and black slicers in the defect signal producing section. But these white and black slicers may be replaced by a single slicer having a slice level which situates substantially at the middle of the white and black picture levels. In such a case only a single differential amplifier may be used.

In the above explained embodiments use is made of the flying spot scanner tube for scanning the identical portions of two patterns in the raster mode. However the two dimensional scanning mode may be effected by a line scanning device such as a laser scanner with a mirror deflector, a solid state line scanning device. In this case the patterns and the scanning device have to be relatively moved in a direction substantially perpendicular to the line scanning direction.

What is claimed is:

1. An apparatus for detecting defects in patterns, particularly defects in chip patterns of photomasks for use in manufacturing semiconductor integrated circuits comprising means for optically scanning simultaneously identical portions of two patterns to be compared with each other to produce first and second picture signals each corresponding to a respective one of the scanned pattern portions;

means for receiving at least one of said first and second picture signals and producing a contour signal which represents contour regions having a predetermined width along the pattern contours;

means for receiving said first and second picture signals and forming a difference between these picture signals to produce a defect signal; and control means for receiving said contour signals and decreasing a defect detection sensitivity in the contour region of the patterns.

2. An apparatus according to claim 1, wherein said control means decrease the defect detection sensitivity to zero in the contour region.

3. An apparatus according to claim 2, wherein said control means comprise a gate having a signal input connected to the output of said defect signal producing means and a control terminal connected to receive said contour signal, whereby the gate is closed upon the occurrence of the contour signal.

4. An apparatus according to claim 2, the control means comprise a gate having a signal output connected to the input of the defect signal producing means and a control terminal connected to receive the contour signal, whereby the gate is closed upon the occurrence of the contour signal.

5. An apparatus according to claim 1, wherein the defect detection sensitivity is made variable and the control means comprise means for changing the defect detection sensitivity in such a manner that the sensitivity is decreased upon the occurrence of the contour signal.

6. An apparatus according to claim 5, wherein said defect signal producing means comprise first and second defect detectors having high and low defect detection sensitivities, respectively and said control means comprise a change over switch connected to the input of the defect signal producing means, whereby the switch is driven by the contour signal in such a manner that the picture signals are supplied to the second defect detector of low sensitivity when the contour signal is fed to the switch.

7. An apparatus according to claim 5, wherein said defect signal producing means comprise first and second defect detectors having high and low defect detection sensitivities, respectively and said control means comprise a change over switch connected to the output of the defect signal producing means, whereby said switch is controlled by the contour signal in such a manner that upon occurrence of the contour signal the defect signal derived from the second defect detector of low sensitivity is supplied as the output defect signal.

8. An apparatus according to claim 1, wherein one of said patterns is a perfect sample pattern having no defect and the picture signal obtained by scanning the sample pattern is supplied to the contour signal producing means.

9. An apparatus according to claim 1, wherein said optically scanning means comprise a carrier stage on which a specimen having a number of identical patterns is place and an optical system for projecting scanning light spots simultaneously onto two adjacent patterns to be compared with each other to produce said first and second picture signals and both the first and second picture signals are supplied to said contour signal producing means.

10. An apparatus according to claim 9, wherein said contour signal producing means comprise first and second delay circuits (52A, 52B; 62A, 62B) having a delay time corresponding to the width of the contour region for delaying said first and second picture signals, respectively; first, second, third and fourth inverters (54A, 56A, 54B, 56B; 64A, 66A, 64B, 66B); a first AND gate (53A; 63A) for receiving the delayed and non-inverted first picture signal from the first delay circuit and the non-delayed and inverted first picture signal from the first inverter; a second AND gate (55A; 65A) for receiving the non-delayed and non-inverted first picture signal and the delayed and inverted first picture signal from the second inverter; a third AND gate (53B; 63B) for receiving the delayed and non-inverted second picture signal and the non-delayed and inverted second picture signal from the third inverter; a fourth AND gate (55B; 65B) for receiving the non-delayed and non-inverted second picture signal and the delayed and inverted second picture signal from the fourth inverter; first and second OR gates (57A, 57B; 67A, 67B) connected to outputs of the first and second AND gates and the third and fourth AND gates, respectively; and an AND gate (58; 68) connected to the outputs of the first and second OR gates.

11. An apparatus according to claim 10, wherein said scanning means scan the patterns in the two dimensional scanning mode and the delay time of said first and second delay circuits is set to a fraction of a horizontal line scanning period (H) so as to produce a horizontal contour signal.

12. An apparatus according to claim 11, wherein said contour signal producing means further comprise thrid and fourth delay circuits (61A, 61B) each having a delay time shorter than that of the first and second delay circuits and the picture signals delayed by the third and fourth delay circuits, respectively are supplied to the defect signal producing means.

13. An apparatus according to claim 12, wherein said delay time of the third and fourth delay circuits is set substantially to a half of the delay time of the first and second delay circuits.

14. An apparatus according to any one of claims 10, 11, 12 and 13, wherein the delay time of the first and second delay circuits is set to an integer multiple of the horizontal line scanning period so as to produce a vertical contour signal.

15. An apparatus according to claim 14, wherein the vertical contour signal producing means further comprise third and fourth delay circuits having a delay time which is equal to an integer multiple of the horizontal line scanning period, but is shorter than the delay time of the first and second delay circuits, and the picture signals delayed by the third and fourth delay circuits are supplied to the defect signal producing means.

16. An apparatus according to claim 15, wherein said vertical contour signal producing section further comprises third and fourth delay circuits (51A, 51B) having a delay time substantially equal to a half of that of the first and second delay circuits (52A, 52B).

17. An apparatus according to claim 10, wherein the apparatus further comprises picture signal converting means for receiving the first and second picture signals supplied from the optically scanning means and converting them into bivalent picture signals and the delay circuits provided in the contour signal producing means are formed by digital delay circuits.

18. An apparatus according to claim 17, wherein said picture signal converting means comprise first and second slicer circuit sections and first and second signal processing circuits each of which comprises a flip-flop having a priority succession.

19. An apparatus according to claim 18, wherein said slicer circuit section comprises a white slicer circuit for slicing the amplitude of the picture signal with a white slicing level which is close to the white picture level and a black slicer circuit for slicing the amplitude of the picture signal with a black slicing level which is close to the black picture level.

20. An apparatus according to claim 1, wherein said defect signal producing means comprise first and second slicer circuits for slicing the amplitudes of the first and second picture signals, respectively with given slicing levels and a differential amplifier for producing a difference between the output signals from the first and second slicer circuits to produce the defect signal.

21. An apparatus according to claim 1, wherein said defect signal producing means comprise first and second white slicer circuits (71A, 71B) for slicing the amplitude of the delayed first and second picture signals, respectively with a white slicing level near the white picture level; a first and second black slicer circuits (72A, 72B) for slicing the amplitude of the delayed first and second picture signals, respectively with a black slicing level close to the black picture level; first and second differential amplifiers (73, 74) for producing a difference between output signals from the first and second white slicer circuits and a difference between output signals from the first and second black slicer circuits; and an OR gate (77) for receiving the output signals from the first and second differential amplifiers and producing the defect signal.

22. An apparatus according to claim 1, wherein said defect signal producing means comprise a differential amplifier (91) for producing a difference between the first and second picture signals; a logic circuit (95, 96, 97) for receiving the first and second picture signals and producing a logic sum signal of the inverted first and second picture signals; a first mixer circuit (92) for receiving the output from the differential amplifier and said logic sum signal; a second mixer circuit (94) for receiving the output signal from the differential amplifier through an inverter; first and second slicer circuits (98, 99) for slicing the amplitude of the output signals from the first and second mixer circuits with slicing levels which are close to their base level; and an OR gate (100) for receiving the output signals from said first and second slicer circuits and producing the defect signal.

23. An apparatus according to claim 1, further comprises defect limiting means connected to the output of the defect signal producing means for receiving the defect signal and removing any defect which is smaller than a predetermined dimension.

24. An apparatus according to claim 23, wherein said defect limiting means comprise at least one delay circuit for delaying the defect signal by a delay time corresponding to said predetermined dimension and at least one AND gate for receiving the delayed and non-delayed defect signals.

* * * * *